United States Patent
Zhang et al.

(10) Patent No.: US 11,857,693 B2
(45) Date of Patent: Jan. 2, 2024

(54) MEDICAL SEALANT GLUE CAPABLE OF PROMOTING WOUND HEALING AND PREPARATION METHOD THEREOF

(71) Applicant: Shandong Branden Medical Device Co.,Ltd, Shandong (CN)

(72) Inventors: Haijun Zhang, Shandong (CN); Kunshan Yuan, Shandong (CN); Rumeng Wang, Shandong (CN); Shoutao Lu, Shandong (CN); Liming Liu, Shandong (CN); Wenrui Cao, Shandong (CN); Chao Zhou, Shandong (CN); Yuxia Yin, Shandong (CN); Wenbo Hou, Shandong (CN); Cuihai Duan, Shandong (CN); Guang Liu, Shandong (CN)

(73) Assignee: Shandong Branden Medical Device Co., Ltd, Shandong (CN)

( * ) Notice: Subject to any disclaimer, the term of this patent is extended or adjusted under 35 U.S.C. 154(b) by 686 days.

(21) Appl. No.: 17/041,462

(22) PCT Filed: Nov. 22, 2019

(86) PCT No.: PCT/CN2019/120078
§ 371 (c)(1),
(2) Date: Sep. 25, 2020

(87) PCT Pub. No.: WO2020/134757
PCT Pub. Date: Jul. 2, 2020

(65) Prior Publication Data
US 2021/0361824 A1    Nov. 25, 2021

(30) Foreign Application Priority Data
Dec. 27, 2018 (CN) .......................... 201811615454.4

(51) Int. Cl.
*A61K 36/00* (2006.01)
*A61L 24/04* (2006.01)
*A61K 35/28* (2015.01)
*A61L 24/00* (2006.01)

(52) U.S. Cl.
CPC ............ *A61L 24/043* (2013.01); *A61K 35/28* (2013.01); *A61L 24/0005* (2013.01)

(58) Field of Classification Search
None
See application file for complete search history.

(56) References Cited

U.S. PATENT DOCUMENTS

2007/0031498 A1   2/2007   Zong et al.
2010/0297235 A1   11/2010  Hnojewyj

FOREIGN PATENT DOCUMENTS

| CN | 102911493 | 2/2013 |
| CN | 104399109 | 3/2015 |
| CN | 105778124 | 7/2016 |
| CN | 107206119 | 9/2017 |
| CN | 108014365 | 5/2018 |
| CN | 109568641 | 4/2019 |

OTHER PUBLICATIONS

"International Search Report (Form PCT/ISA/210) of PCT/CN2019/120078," dated Feb. 19, 2020, with English translation thereof, pp. 1-5.

*Primary Examiner* — Russell G Fiebig
(74) *Attorney, Agent, or Firm* — JCIPRNET

(57) ABSTRACT

The disclosure provides a medical sealant glue capable of promoting wound healing and a preparation method thereof. The medical sealant glue is formed by covalent cross-linking of two components after being physically mixed by a mixing tool, wherein the first component is a nucleophilic component, and the second component is an electrophilic component. The medical sealant glue has a gelation time of 1-10 s, a swelling ratio of 0-100%, a bursting strength of 100-250 mmHg, and a degradation time of 0.5-300 days. The nucleophilic component of the medical sealant glue contains exosome or hyaluronic acid and chitosan, and thus the medical sealant glue not only has the effect of promoting wound healing, but also has antibacterial and anti-infection effects.

17 Claims, No Drawings

MEDICAL SEALANT GLUE CAPABLE OF PROMOTING WOUND HEALING AND PREPARATION METHOD THEREOF

CROSS-REFERENCE TO RELATED APPLICATION

This application is a 371 of international application of PCT application serial no. PCT/CN2019/120078, filed on Nov. 22, 2019, which claims the priority benefit of China application no. 201811615454.4, filed on Dec. 27, 2018. The entirety of each of the above mentioned patent applications is hereby incorporated by reference herein and made a part of this specification.

BACKGROUND

Technical Field

The present invention belongs to the technical field of medical sealant glue, specifically relates to a medical sealant glue capable of promoting wound healing and a preparation method thereof. The medical sealant glue of the application not only has the effect of promoting wound healing, but also has antibacterial and anti-infection effects.

Description of Related Art

In surgery, fast, effective and safe tissue closure is one of the key factors to ensure the success of surgery. Excellent medical sealant glues can control blood leakage or tissue fluid on the wound surface, ensure a clear surgical field of vision, improve surgical efficiency and accelerate postoperative recovery of patients.

A variety of medical sealant glues have been developed at home and abroad, mainly including animal-derived medical glues, semi-synthetic medical glues and synthetic medical glues, wherein the animal-derived medical glues are divided into thrombin-containing fibrin glue (e.g., Porcine Fibrin Sealant Kit and Fibrin Sealant (Human)) and collagen as well as gelatin (e.g., fluid gelatin (surgiflo)); the semi-synthetic medical glues are divided into gelatin-resorcinol formaldehyde/glutaraldehyde (e.g., Gluetiss) and bovine serum albumin/glutaraldehyde (e.g., Bioglue); the synthetic medical glues include α-cyanoacrylates (e.g., Compont medical glue and Baiyun medical glue, etc.) and polyethylene glycols (e.g., Duraseal and Adherus). Wherein, the raw materials of animal-derived medical glues are extracted from human or animals (pig or cow), they are of animal origin, and there is a risk of transmission of potential animal diseases such as mad cow disease. Semi-synthetic medical glues typically contain glutaraldehyde cross-linking agent. Glutaraldehyde is a toxic stationary liquid and is used for preservation and preparation of electron microscope samples of cell and tissue samples. Therefore, semi-synthetic medical glues have a risk of poor biocompatibility. For synthetic medical glues, there would be a lot of heat generated during cross-linking of α-cyanoacrylates medical glues, which is prone to initiate inflammation. The formed glue film is hard, its degradation time is long, and toxic side products (e.g., formaldehyde) may form during the process of degradation, which may cause inflammation and thus delay wound healing.

In recent years, the development of polyethylene glycol medical sealant glues has attracted more and more attention. For example, Patent application No. 201610168941.5 discloses a biodegradable medical hydrogel formed by in-situ crosslinking. The hydrogel has a gelation time of less than 20 seconds, a swelling ratio of 0-600%, and a bursting strength not less than 50 mmHg. It starts to degrade within 3-40 days, and the degradation time is 7-180 days. Raw materials for preparing the hydrogel comprise a combination of a first component containing nucleophilic functional groups and a second component containing electrophilic functional groups, and the hydrogel is formed by covalent cross-linking of two components after being physically mixed by a mixing tool. The physical properties and biological degradability of hydrogel in the invention can be adjusted by changing the proportion of the composition of the first component or the second component. Hydrogel can be used in different parts of the biological environment due to its controllable properties and simple operation. Hydrogel is widely used in dura mater (endocranium) sealing, blood vessel sealing, eye bandage, hernia repair, anti-adhesion, pneumonectomy sealing, intestinal anastomosis sealing, etc. However, the hydrogel is simply water-sealing and can promote wound healing, but the speed of wound healing is slow, and it does not have antibacterial and anti-infection effects.

Patent application No. 201410691792.1 discloses a gel hemostatic material and a preparation method thereof. The hemostatic material works through a cross-linking reaction between an oligomer of nucleophilic polymers and amino acids and an electrophilic polymer to in situ generate a body type polymer to achieve the effect of blocking and hemostasis. For the hemostatic material composition and the preparation method thereof in this application, the proportion of raw materials can be precisely controlled to achieve a reasonable gelation time less than 10 seconds; and the formed biogel hemostatic material will have a desired high strength, it is determined to have an elongation at break of 300-600% and a compressive strength greater than 3 Mpa; and the requirements of surgery can be better satisfied. The hemostatic material has such advantages as in-situ cross-linking forming, mild reaction conditions, tunable gelation rates, low dilatability, and high adhesive strength. However, this hemostatic material still has the disadvantages of low wound healing speed and not effective in inhibiting microbial and preventing infection.

The current commercially available polyethylene glycol hydrogel products, for example, Duraseal and Adherus, also have the disadvantages of low wound healing speed and not effective in inhibiting microbial and preventing infection.

To sum up, there is an urgent need clinically for a medical sealant with good biocompatibility, which has good gelation time, good softness and high strength, and is capable of promoting wound healing and has anti-infection effects.

SUMMARY

The present invention aims to provide an in-situ cross-linking formed medical sealant glue which has advantages of mild reaction conditions, tunable gelation rates, low swelling ratio, and high adhesive strength, and also has the effects of promoting wound healing and preventing wound infection.

The present invention can be achieved through the following technical scheme:

A medical sealant glue capable of promoting wound healing. Raw materials for preparing the medical sealant glue include a first component containing nucleophilic functional groups and a second component containing electrophilic functional groups, wherein the first component is composed of a) dendritic molecules, b) exosome or hyaluronic acid and c) chitosan, and the second component is active polyethylene glycol.

The dendritic molecules are one or more of dendritic polyethylene imine, dendritic polypropylene imine, dendritic poly-L-lysine and dendritic polyamide.

The exosome is exosome secreted from one or several of adipose-derived mesenchymal stem cells, placenta-derived mesenchymal stem cells and bone marrow mesenchymal stem cells.

The chitosan is one or more of chitosan hydrochloride, chitosan acetate and chitosan lactate.

The active polyethylene glycol is one or more of two-arm N-hydroxysuccinimide succinate-based polyethylene glycol (2-arm-PEG-SS), two-arm N-hydroxysuccinimide glutarate-based polyethylene glycol (2-arm-PEG-SG), two-arm N-hydroxysuccinimide adipate-based polyethylene glycol (2-arm-PEG-SA) and two-arm N-hydroxysuccinimide sebacate-based polyethylene glycol (2-arm-PEG-SSeb).

The dendritic molecules have molecular weights of 1500-2500 Dalton.

The hyaluronic acid has a molecular weight of 3 KDa-2200 KD.

The active polyethylene glycol has a molecular weight of 3000-4000 Dalton, and a concentration of 100-300 mg/mL.

The molar ratio of active functional groups between the first component and the second component is 0.75-1.25.

The medical sealant glue has a gelation time of 1-10 s, a swelling ratio of 0-100%, a bursting strength of 100-250 mmHg, and a degradation time of 0.5-300 days.

The invention further provides a method for preparing the medical sealant glue capable of promoting wound healing, in which the first component containing nucleophilic functional groups is dissolved in a buffer solution at pH 7-12 to obtain a solution A; the second component containing electrophilic functional groups is dissolved in a buffer solution at pH 2-8 to obtain a solution B; the solution A and the solution B are then mixed so that the first component and the second component crosslink to form the medical sealant glue.

In the preparation method, the buffer solution is formulated from one or more of phosphate, carbonate, borate, phosphoric acid, acetic acid, hydrochloric acid, sodium hydroxide and the like; and the buffer solution has a concentration of 0.01-0.1 mol/L.

The components used in the invention are all commercialized products, the structures and compositions of which are also known to persons skilled in the art.

The nucleophilic component of the invention contains exosome secreted from mesenchymal stem cells or hyaluronic acid, and also contains chitosan. The exosome and chitosan both contain active amino groups which can crosslink with the electrophilic component to form a network structure. Hyaluronic acid can be physically wound with the polymer in the gel to enhance the mechanical properties of the gel, thus forming a hydrogel having advantages of rapid gelling speed, mild reaction conditions, a stable structure, etc. Moreover, exosome or hyaluronic acid can promote wound healing rapidly, and chitosan has anti-bacterial and anti-infection effects. The dendritic molecules in the nucleophilic component can increase the crosslinking point of the reaction and form hydrogels with stronger mechanical properties, of which the bursting strength can reach over 100 mmHg. The medical sealant glue capable of promoting wound healing in the present invention will play an important role in the medical field and has a broad application prospect.

DESCRIPTION OF THE EMBODIMENTS

The technical scheme of the present invention will be further illustrated in detail in combination with embodiments and comparative examples as below, but the invention is not limited to these specific embodiments. Methods used in the embodiments are ordinary methods, unless otherwise specifically illustrated. Hydrogels are detected by the following detection methods in the invention.

Detection of Gelation Time:

(1) Preparation of samples to test: The first component containing nucleophilic functional groups is dissolved in a buffer solution at pH 7-12 to obtain a solution A, which is transferred into one syringe of a two-component mixer. The second component containing electrophilic functional groups is then dissolved in a buffer solution at pH 2-8 to obtain a solution B, which is transferred into the other syringe of the two-component mixer. The two-component mixer is installed for standby use. (2) Detection of gelation time: The two-component mixer is pushed evenly. The solution A and the solution B are sprayed onto a watch glass after being mixed in the two-component mixer. Timing is started at the same time until a gel is formed completely (no flowing liquid), the time is recorded as the gelation time.

Detection of Swelling Ratio:

Swelling ratio refers to the percentage increase in mass when swelling saturation is achieved in PBS solution after effective cross-linking of the hydrogel. It is determined following the steps below: (1) Preparation of samples to test: The solution A and the solution B are charged onto the two-component mixer and injected into a watch glass to form a gel according to the preparation method of samples to test as described in the above detection of gelation time. The resulting gel is cut into cubic gel of 1 cm*1 cm*1 cm. The hydrogel samples are precisely weighed. (2) A PBS buffer solution at pH 7.4 is formulated. (3) Detection of swelling ratio: samples prepared in (1) are transferred into a ground triangular flask, into which is also added the PBS solution at pH 7.4 which has been preheated to 37±1° C. The amount of the PBS solution is at least 40 times the mass of the samples. The ground triangular flask containing samples is then transferred into an incubator at 37±1° C. 24 h later, samples are taken out and removed the surface moisture with a filter paper, and weighed. The swelling ratio of the gel is calculated following the formula below.

Swelling ratio of gel=(sample weight after swelling−sampling amount)/sampling amount×100%

Detection of Bursting Strength:

In addition to the gelation time and the swelling ratio, the bursting strength of hydrogel is also an important index of the material, which reflects the mechanical properties of the hydrogel during use. The detection method is as below:

(1) Taking fresh hog casing, in which a hole with a diameter of about 0.16 cm±0.02 cm is cut, ready for use.

(2) The solution A and the solution B are charged onto the two-component mixer according to the preparation method of samples to test as described in the above detection of gelation time.

(3) The two-component mixer is pushed to form a hydrogel of specified thickness on the hole of the casing; after the gel is formed completely, pressure is applied evenly under the casing until the gel is broken or peeled off, and the maximum pressure is recorded.

Detection of Degradation Time In Vitro:

(1) Preparation of samples to test: The solution A and the solution B are charged onto the two-component mixer and injected into a watch glass to form a gel according to the preparation method of samples to test as described in the above detection of gelation time. The resulting gel is cut into cubic gel of 1 cm*1 cm*1 cm.

(2) A PBS buffer solution at pH 7.4 is formulated.

(3) Detection of degradation time in vitro: the samples prepared in (1) are placed into a closed container with a PBS buffer solution, and transferred into an incubator at 37±1° C.

The change of samples in the buffer solution is observed until it is invisible to the naked eyes, that is, the degradation time of the gel in vitro.

Cytotoxicity Test:

The solution A and the solution B are charged onto the two-component mixer and injected into a watch glass to form a gel according to the preparation method of samples to test as described in the above detection of gelation time. Except for the swelling absorption capacity, extraction is conducted by adding 1.0 ml extracting medium per 0.1 g, in which the extracting medium is an MEM culture medium containing serum, the extracting temperature is 37±1° C., and the extracting time is 24±2 h. The cytotoxicity test is performed with the extract as the test solution according to the test method specified in GB/T16886.5-2017, and rated according to United States Pharmacopeia.

Intradermal Reaction Test:

The solution A and the solution B are charged onto the two-component mixer and injected into a watch glass to form a gel according to the preparation method of samples to test as described in the above detection of gelation time. Except for the swelling absorption capacity, extraction is conducted by adding 1.0 ml extracting medium per 0.1 g, in which the extracting medium is saline and cottonseed oil, the extracting temperature is 37±1° C., and the extracting time is 72±2 h. The intradermal reaction test is performed with the extract as the test solution according to the test method specified in GB/T 16886.10-2017.

Acute Systemic Toxicity Test:

The solution A and the solution B are charged onto the two-component mixer and injected into a watch glass to form a gel according to the preparation method of samples to test as described in the above detection of gelation time. Except for the swelling absorption capacity, extraction is conducted by adding 1.0 ml extracting medium per 0.1 g, in which the extracting medium is saline and cottonseed oil, the extracting temperature is 37±1° C., and the extracting time is 72±2 h. The acute systemic toxicity test is performed with the extract according to the test method for intraperitoneal injection specified in GB/T 16886.11-2011.

Antibacterial Test:

The bacterial suspension is in direct contact with the antibacterial products. The antibacterial rate is calculated to determine whether the antibacterial products have antibacterial capacities. Bacteria: *Staphylococcus aureus, Escherichia coli, Pseudomonas aeruginosa*.

Preparation of Medical Sealant Glue Capable of Promoting Wound Healing

Embodiments 1-9 and comparative examples 1-3, following the mass ratios shown in Tables 1-1 and 1-2 below, the first component containing nucleophilic functional groups is dissolved in buffer solutions at different pH values as shown in Table 1-2 below to obtain the solution A, which is transferred into one syringe of a two-component mixer, and the second component containing electrophilic functional groups is then dissolved in buffer solutions at different pH values as shown in Table 1-2 below to obtain the solution B, which is transferred into the other syringe of the two-component mixer. The two-component mixer is installed, and a nozzle is installed on it to push the two-component mixer and eject the liquid in the two syringes after being mixed in the two-component mixer, thus rapidly forming the medical sealant glue capable of promoting wound healing.

TABLE 1-1

The composition of the medical sealant glue capable of promoting wound healing

| Composition of the sealant glue | | Embodiment 1 | Embodiment 2 | Embodiment 3 | Embodiment 4 | Embodiment 5 | Embodiment 6 | Embodiment 7 |
|---|---|---|---|---|---|---|---|---|
| First component (mg) | Dendritic polyethylene imine (1500 Dalton) | | 8.5 | | | 4 | | 9 |
| | Dendritic polypropylene imine (2500 Dalton) | | | 26 | | 4.5 | 10 | |
| | Dendritic poly-L-lysine (2000 Dalton) | 13 | | | 6.5 | | 10 | |
| | Dendritic polyamide (2000 Dalton) | | | | 6.5 | | | 9 |
| | Adipose-derived mesenchymal stem cells | 0.5 | | | | | | 0.5 |
| | Placenta-derived mesenchymal stem cells | | 0.3 | | | | | |
| | Bone marrow mesenchymal stem cells | | | 1.0 | | | | |
| | Hyaluronic acid | | | | | 0.5 | 0.3 | 1.0 |
| | Chitosan hydrochloride | 1.5 | | | | | 0.6 | 1.5 |
| | Chitosan acetate | | 1.2 | | 0.75 | 0.6 | | 1.5 |
| | Chitosan lactate | | | 3.0 | 0.75 | | 1.5 | |

TABLE 1-1-continued

The composition of the medical sealant glue capable of promoting wound healing

| | Composition of the sealant glue | Embodiment 8 | Embodiment 9 | Comparative example 1 | Comparative example 2 | Comparative example 3 |
|---|---|---|---|---|---|---|
| First component (mg) | Dendritic polyethylene imine (1500 Dalton) | | 13 | 13 | 20 | 14.5 |
| | Dendritic polypropylene imine (2500 Dalton) | 6.5 | | | | |
| | Dendritic poly-L-lysine (2000 Dalton) | | | | | |
| | Dendritic polyamide (2000 Dalton) | 6.5 | | | | |
| | Adipose-derived mesenchymal stem cells | | 0.5 | 0.5 | 0.5 | 0.5 |
| | Placenta-derived mesenchymal stem cells | | | | | |
| | Bone marrow mesenchymal stem cells | | | | | |
| | Hyaluronic acid | 0.5 | | | | |
| | Chitosan hydrochloride | | 1.5 | 1.5 | | 1.5 |
| | Chitosan acetate | | | | | |
| | Chitosan lactate | 1.5 | | | | |

TABLE 1-2

The composition of the medical sealant glue capable of promoting wound healing

| Composition of the sealant glue | | Embodiment 1 | Embodiment 2 | Embodiment 3 | Embodiment 4 | Embodiment 5 | Embodiment 6 | Embodiment 7 |
|---|---|---|---|---|---|---|---|---|
| Second component (mg) | (2-arm-PEG-SS) (3000 Dalton) | | | 300 | | 50 | | |
| | (2-arm-PEG-SG) (4000 Dalton) | | 100 | | | 50 | | 75 |
| | (2-arm-PEG-SA) (3500 Dalton) | | | | 75 | | 150 | 75 |
| | (2-arm-PEG-SSet) (3500 Dalton) | 150 | | | 75 | | 150 | |
| Buffer solutions for the second component (pH) | | 4 | 4 | 2 | 4 | 4 | 4 | 4 |
| Buffer solutions for the first component (pH) | | 10 | 12 | 7 | 10 | 10 | 10 | 10 |

| | Composition of the sealant glue | Embodiment 8 | Embodiment 9 | Comparative example 1 | Comparative example 2 | Comparative example 3 |
|---|---|---|---|---|---|---|
| Second component (mg) | (2-arm-PEG-SS) (3000 Dalton) | 150 | | | | |
| | (2-arm-PEG-SG) (4000 Dalton) | | | | | |
| | (2-arm-PEG-SA) (3500 Dalton) | | | | | |
| | (2-arm-PEG-SSet) (3500 Dalton) | | 150 | 150 | 150 | 150 |

TABLE 1-2-continued

| The composition of the medical sealant glue capable of promoting wound healing | | | | | |
|---|---|---|---|---|---|
| Buffer solutions for the second component (pH) | 4 | 7.4 | 4 | 4 | 4 |
| Buffer solutions for the first component (pH) | 10 | 7.4 | 13 | 10 | 10 |

The physicochemical properties and biological properties of the medical sealant glue are detected respectively according to the processes for detecting the gelation time, the swelling ratio, the bursting strength, and the degradation time in vitro, the cytotoxicity test, the intradermal reaction test, the acute systemic toxicity test and the antibacterial test, with the results shown in Table 2 and Table 3.

TABLE 2

| Detection results of the sealant glue | Embodiment 1 | Embodiment 2 | Embodiment 3 | Embodiment 4 | Embodiment 5 | Embodiment 6 | Embodiment 7 |
|---|---|---|---|---|---|---|---|
| Gelation time (s) | 1 | 5 | 10 | 1 | 1 | 1 | 1 |
| Swelling ratio (%) | 20 | 100 | 35 | 25 | 95 | 10 | 48 |
| Bursting strength (mmHg) | 220 | 100 | 250 | 215 | 115 | 245 | 231 |
| Degradation time (days) | 125 | 2 | 1.5 | 110 | 1.5 | 300 | 0.5 |
| Cytotoxicity | Grade 1 | Grade 1 | Grade 1 | Grade 1 | Grade 1 | Grade 1 | Grade 1 |
| Intradermal reaction | Grade 1 | Grade 1 | Grade 1 | Grade 1 | Grade 1 | Grade 1 | Grade 1 |
| Acute systemic toxicity (Yes or No) | No | No | No | No | No | No | No |

| Detection results of the sealant glue | Embodiment 8 | Embodiment 9 | Comparative example 1 | Comparative example 2 | Comparative example 3 |
|---|---|---|---|---|---|
| Gelation time (s) | 1 | 7.5 | Ungelled | 0.5 | 1 |
| Swelling ratio (%) | 31 | 23 | / | 125 | 45 |
| Bursting strength (mmHg) | 220 | 218 | / | 215 | 212 |
| Degradation time (days) | 2 | 120 | / | 0.25 | 120 |
| Cytotoxicity | Grade 1 | Grade 1 | / | Grade 1 | Grade 1 |
| Intradermal reaction | Grade 1 | Grade 1 | / | Grade 1 | Grade 1 |
| Acute systemic toxicity (Yes or No) | No | No | / | No | No | medical sealant glue is related to the concentration of the nucleophilic component and the electrophilic component. This is because that, with the increase of the concentration of the nucleophilic component and the electrophilic component, the formed network structure becomes denser, and there are more crosslinking points, so that the medical sealant glue has greater bursting strength.

As can be seen from the data in the table above, the gelation time of the medical sealant glue is mainly related to pH values of the acidic buffer solution and the basic buffer solution. When the concentration and proportion of the nucleophilic component and the electrophilic component are in certain ranges, the pH of the acidic buffer solution is 4, and the pH of the basic buffer solution is 10, the medical sealant glue can gelatinize within 1 s. The comparison of Embodiments 1-9 shows that, the bursting strength of the The comparison of Embodiments 1-9 shows that, the swelling ratio and the degradation time of the medical sealant glue are related to polyethylene glycol-modified functional groups, the concentration of the nucleophilic component, the concentration of the electrophilic component, and the ratio of the two components. As the length of hydrophobic chain segments of polyethylene glycol-modified functional groups increases, the swelling ratio of the medical sealant glue decreases gradually, and the degradation time extends gradually, too; as the concentration of the nucleophilic component and the electrophilic component increases, the swelling ratio of the medical sealant glue decreases gradually, and the degradation time extends gradually, too. The comparison of Embodiments 1-9 and Comparative example 2 shows that, as the remaining active amino component in the system increases, the swelling ratio of the medical sealant glue increases gradually, and the degradation time is gradually reduced. It is known from Comparative example 1 that, when the pH values of the acidic buffer solution and the basic buffer solution are not in the specified ranges, the medical sealant glue is unable to gelatinize.

The comparison of Embodiments 1-9 and Comparative examples 1-3 shows that, the medical sealant glue has a good biocompatibility. The cytotoxicity test, the intradermal reaction test and the acute systemic toxicity test of the medical sealant glue all conform to the biocompatibility requirement of the medical sealant glue.

wound once a day; and mice in the control group were sprayed with saline at the same amount as that of the medical sealant glue used in the test group once a day. The profile of wound healing was observed within 20 days.

Determination of Skin Wound Healing Rate in Mice

The wounds of the mice were photographed every two days after the injury. The wound area of mice was calculated with Image-Pro Plus Version 6.0, until the wounds heal.

Healing rate=(Original wound area−Unhealed wound area)/Original wound area×100%

Standard of wound healing (complete epithelialization of the wound surface): healing area is greater than 95% of the original wound area, or the wound area is less than 5% of the original wound area, that is, complete healing.

The profile of skin wound healing in mice of the control group and the test group is shown in Table 4.

TABLE 3

Detection results of the medical sealant glue capable of promoting wound healing

| Detection results of the sealant glue | | Embodiment 1 | Embodiment 2 | Embodiment 3 | Embodiment 4 | Embodiment 5 | Embodiment 6 | Embodiment 7 |
|---|---|---|---|---|---|---|---|---|
| Antibacterial Test (Yes or No) | *Staphylococcus aureus* | Yes | Yes | Yes | Yes | Yes | Yes | Yes |
| | *Escherichia coli* | Yes | Yes | Yes | Yes | Yes | Yes | Yes |
| | *Pseudomonas aeruginosa* | Yes | Yes | Yes | Yes | Yes | Yes | Yes |

| Detection results of the sealant glue | | Embodiment 8 | Embodiment 9 | Comparative example 1 | Comparative example 2 | Comparative example 3 |
|---|---|---|---|---|---|---|
| Antibacterial Test (Yes or No) | *Staphylococcus aureus* | Yes | Yes | / | Yes | No |
| | *Escherichia coli* | Yes | Yes | / | Yes | No |
| | *Pseudomonas aeruginosa* | Yes | Yes | / | Yes | No |

The comparison of Embodiments 1-9 and Comparative example 3 in Table 3 shows that, the medical sealant glue has antibacterial effect only when it contains chitosan.

Skin Wound Healing Test in Mice

Test Grouping and Test Method

36 SPF male Kunming mice with a weight range of 18-22 g were randomly divided into two groups, 18 mice in each group, including a control group and a test group. After 1 week of adaptive feeding, a skin wound model of mice was established as below: mice were anesthetized with ether, and sheared at the back; the back side hair was shaved clean with a razor, and then the skin was cleaned and disinfected with 70% ethanol. Circular marks each slightly larger than 1 cm in diameter were made respectively at the left and right sides of the spine at the same location. Under aseptic conditions, a skin biopsy punch with a diameter of 1 cm is used to create a full-thickness skin wound within the circular mark. After modeling, the wounds were exposed, and the mice were fed separately. The day of injury was recorded as day 0. After successful modeling, mice in the test group were sprayed with the medical sealant glue of Embodiment 1 on the skin

TABLE 4

Effect of the medical sealant glue capable of promoting wound healing on the skin wound healing rate in mice

| | Wound healing rate (%) | |
|---|---|---|
| Days | Control Group | Test Group |
| 2 | 7.41 ± 0.87 | 9.54 ± 0.81 |
| 4 | 14.85 ± 1.68 | 20.23 ± 1.14 |
| 6 | 21.45 ± 2.23 | 32.56 ± 2.53 |
| 8 | 33.68 ± 3.93 | 59.47 ± 4.96 |
| 10 | 75.42 ± 2.37 | 94.62 ± 2.04 |
| 12 | 80.27 ± 2.95 | 96.87 ± 1.45 |
| 14 | 84.51 ± 2.54 | / |
| 16 | 88.76 ± 3.72 | / |
| 18 | 91.55 ± 3.42 | / |
| 20 | 92.86 ± 1.48 | / |

It can be seen from Table 4 that, for the mice treated with the medical sealant glue capable of promoting wound healing, the healing rate achieved more than 95% on day 12, at which the wound has been healed; while for the mice in the control group, the healing rate is still below 95% on day 20, at which the wound has not been healed. Hence, it can be seen that the medical sealant glue capable of promoting wound healing of the invention has the effect of promoting wound healing.

The above disclosures are only several specific embodiments of the invention, but the invention is not limited thereto. Any change that can be considered by persons skilled in the art shall fall within the protection scope of the present invention.

What is claimed is:

1. A medical sealant glue capable of promoting wound healing, wherein: the medical sealant glue comprise a crosslinked compound of a first component containing nucleophilic functional groups and a second component containing electrophilic functional groups, wherein the first component is composed of:
   dendritic molecules;
   exosome or hyaluronic acid; and
   chitosan, and the second component is active polyethylene glycol.

2. The medical sealant glue capable of promoting wound healing according to claim 1, wherein: the dendritic molecules are one or more of dendritic polyethylene imine, dendritic polypropylene imine, dendritic poly-L-lysine and dendritic polyamide.

3. The medical sealant glue capable of promoting wound healing according to claim 1, wherein: the exosome is exosome secreted from one or several of adipose-derived mesenchymal stem cells, placenta-derived mesenchymal stem cells and bone marrow mesenchymal stem cells.

4. The medical sealant glue capable of promoting wound healing according to claim 1, wherein: the chitosan is one or more of chitosan hydrochloride, chitosan acetate and chitosan lactate.

5. The medical sealant glue capable of promoting wound healing according to claim 1, wherein: the active polyethylene glycol is one or more of two-arm N-hydroxysuccinimide succinate-based polyethylene glycol, two-arm N-hydroxysuccinimide glutarate-based polyethylene glycol, two-arm N-hydroxysuccinimide adipate-based polyethylene glycol and two-arm N-hydroxysuccinimide sebacate-based polyethylene glycol.

6. The medical sealant glue capable of promoting wound healing according to claim 1, wherein: the dendritic molecules have molecular weights of 1500-2500 Dalton.

7. The medical sealant glue capable of promoting wound healing according to claim 1, wherein: the active polyethylene glycol has a molecular weight of 3000-4000 Dalton, and a concentration of 100-300 mg/mL.

8. The medical sealant glue capable of promoting wound healing according to claim 1, wherein: a molar ratio of active functional groups between the first component and the second component is 0.75-1.25.

9. A preparation method for the medical sealant glue capable of promoting wound healing according to claim 1, comprising the steps of: dissolving a first component containing nucleophilic functional groups in a buffer solution at pH 7-12 to obtain a solution A; dissolving a second component containing electrophilic functional groups in the buffer solution at pH 2-8 to obtain a solution B; and mixing the solution A and the solution B so that the first component and the second component crosslink to form the medical sealant glue.

10. The preparation method according to claim 9, wherein: the buffer solution is formulated from one or more reagent of phosphate, carbonate, borate, phosphoric acid, acetic acid, hydrochloric acid and sodium hydroxide; and the buffer solution has a concentration of 0.01-0.1 mol/L.

11. A preparation method for the medical sealant glue capable of promoting wound healing according to claim 2, comprising the steps of: dissolving a first component containing nucleophilic functional groups in a buffer solution at pH 7-12 to obtain a solution A; dissolving a second component containing electrophilic functional groups in the buffer solution at pH 2-8 to obtain a solution B; and mixing the solution A and the solution B so that the first component and the second component crosslink to form the medical sealant glue.

12. A preparation method for the medical sealant glue capable of promoting wound healing according to claim 3, comprising the steps of: dissolving a first component containing nucleophilic functional groups in a buffer solution at pH 7-12 to obtain a solution A; dissolving a second component containing electrophilic functional groups in the buffer solution at pH 2-8 to obtain a solution B; and mixing the solution A and the solution B so that the first component and the second component crosslink to form the medical sealant glue.

13. A preparation method for the medical sealant glue capable of promoting wound healing according to claim 4, comprising the steps of: dissolving a first component containing nucleophilic functional groups in a buffer solution at pH 7-12 to obtain a solution A; dissolving a second component containing electrophilic functional groups in the buffer solution at pH 2-8 to obtain a solution B; and mixing the solution A and the solution B so that the first component and the second component crosslink to form the medical sealant glue.

14. A preparation method for the medical sealant glue capable of promoting wound healing according to claim 5, comprising the steps of: dissolving a first component containing nucleophilic functional groups in a buffer solution at pH 7-12 to obtain a solution A; dissolving a second component containing electrophilic functional groups in the buffer solution at pH 2-8 to obtain a solution B; and mixing the solution A and the solution B so that the first component and the second component crosslink to form the medical sealant glue.

15. A preparation method for the medical sealant glue capable of promoting wound healing according to claim 6, comprising the steps of: dissolving a first component containing nucleophilic functional groups in a buffer solution at pH 7-12 to obtain a solution A; dissolving a second component containing electrophilic functional groups in the buffer solution at pH 2-8 to obtain a solution B; and mixing the solution A and the solution B so that the first component and the second component crosslink to form the medical sealant glue.

16. A preparation method for the medical sealant glue capable of promoting wound healing according to claim 7, comprising the steps of: dissolving a first component containing nucleophilic functional groups in a buffer solution at pH 7-12 to obtain a solution A; dissolving a second component containing electrophilic functional groups in the buffer solution at pH 2-8 to obtain a solution B; and mixing the solution A and the solution B so that the first component and the second component crosslink to form the medical sealant glue.

17. A preparation method for the medical sealant glue capable of promoting wound healing according to claim 8, comprising the steps of: dissolving a first component containing nucleophilic functional groups in a buffer solution at pH 7-12 to obtain a solution A; dissolving a second component containing electrophilic functional groups in the buffer solution at pH 2-8 to obtain a solution B; and mixing the solution A and the solution B so that the first component and the second component crosslink to form the medical sealant glue.

* * * * *